(12) United States Patent (10) Patent No.: US 9,164,098 B2
Albers et al. (45) Date of Patent: Oct. 20, 2015

(54) DETERMINING AN EXPRESSION STATUS OF HUMAN EPIDERMAL GROWTH FACTOR RECEPTOR 2 (HER2) IN A BIOLOGICAL SAMPLE

(75) Inventors: Christian Albers, Bremen (DE); Eckhard Belau, Lilienthal (DE); Sören-Oliver Deininger, Leipzig (DE); Sandra Rauser, Munich (DE); Detlev Suckau, Grasberg (DE); Axel Walch, Baldham (DE)

(73) Assignee: Bruker Daltonik GmbH, Bremen (DE)

( * ) Notice: Subject to any disclaimer, the term of this patent is extended or adjusted under 35 U.S.C. 154(b) by 829 days.

(21) Appl. No.: 12/879,619

(22) Filed: Sep. 10, 2010

(65) Prior Publication Data

US 2011/0059554 A1 Mar. 10, 2011

Related U.S. Application Data

(60) Provisional application No. 61/241,253, filed on Sep. 10, 2009.

(51) Int. Cl.
*G01N 33/483* (2006.01)
*G01N 33/50* (2006.01)
*G01N 33/574* (2006.01)
*G01N 30/72* (2006.01)
*G01N 33/68* (2006.01)

(52) U.S. Cl.
CPC ...... *G01N 33/57484* (2013.01); *G01N 33/6848* (2013.01); *G01N 33/6851* (2013.01); *G01N 2333/71* (2013.01); *G01N 2800/52* (2013.01)

(58) Field of Classification Search
CPC .............. G01N 33/6848; G01N 33/6851
USPC .................................. 435/7.1, 7.2, 7.21, 7.23
See application file for complete search history.

(56) References Cited

U.S. PATENT DOCUMENTS

| 7,452,727 B2 * | 11/2008 | Hennig et al. ............. 436/64 |
| 7,811,778 B2 * | 10/2010 | Goldenring ............. 435/7.23 |
| 2008/0176258 A1 | 7/2008 | Pastorek et al. | |

OTHER PUBLICATIONS

Bulluff, B., et al. The American Journal of Pathology, 179(6): pp. 2720-2729, 2011.*
Rauser, S., et al. J. Proteome Res., 9: 1854-1863, 2010.*
Hao, J., et al., PLoS Comput. Biol. 4(8): 1-10, 2008.*
Gast, M.-C. W., et al. Breast Cancer Res. Treat. 116: 17-29, 2009.*
Pawlik, T.M., et al. Breast cancer Research and Treatment, 89: 149-157, 2005.*
Sjostrom, J., et al. European Journal of Cancer, 38: 535-542, 2002.*
Rozan, S., et al., Int. J. Cancer (Pred. Oncol.) 79:27-33, 1998.*
De Laurentiis, M.D., et al., Clin. Cancer Res., 11(13): 4741-4748, 2005.*
Zhang et al., "Proteomic study reveals that proteins involved in metabolic and detoxification pathways are highly expressed in HER-2/neu-positive breast cancer", Molecular & Cellular Proteomics, vol. 4, No. 11, Nov. 2005, pp. 1686-1696.
Justenhoven et al., "Polymorphic loci of E2F2, CCND1 and CCND3 are associated with HER2 status of breast tumors", International Journal of Cancer, vol. 124, No. 9, May 2009, pp. 2077-2081.
MacKay et al., "CDNA Microarray Analysis of Genes Associated with ERBB2 (HER2/NEU) Overexpression in Human Mammary Luminal Epithelial Cells", Oncogene, Nature Publishing Group, GB, vol. 22, No. 17, pp. 2680-2688, May 2003.
Hao et al., "Identificatoin and Rational Redesign of Peptide Ligands to CRIP1, a Novel Biomarker for Cancers", PLOS Computational Biology 2008, LNKD-PUBMED:18670594, vol. 4, No. 8, p. E1000138, 2008.
Ma et al., "Gene Expression Profiles of Human Breast Cancer Progression", Proceedings of the National Academy of Sciences of the United States of America May 13, 2003 US LNNKD-DOI:10.1073/PNAS.0931261100, vol. 100, No. 10, pp. 5974-5979, May 2003.
Liu et al., "Thiamine Transporter Gene Expression and Exogenous Thiamine Modulate the Expression of Genes Involved in Drug and Prostaglandin Metabolism in Breast Cancer Cells", Molecular Cancer Research: MCR Aug. 2004, LNKD-PUBMED:15328374, vol. 2, No. 8, pp. 477-487.
European Search Report, Nov. 15, 2013.

* cited by examiner

*Primary Examiner* — Misook Yu
*Assistant Examiner* — Anne Holleran
(74) *Attorney, Agent, or Firm* — O'Shea Getz P.C.

(57) ABSTRACT

A method for determining an expression of human epidermal growth factor receptor 2 (HER2) of a subject. The method includes providing a sample from the subject; measuring one of (i) amounts of two or more proteins in the sample, each protein having a molecular weight substantially equal to 4740, 8404, 8419, 8435, 8450, 8455, 8465, 8570, 8607 or 8626 atomic mass units, and (ii) amounts of at least one of human cystein-rich intestinal protein 1 (CRIP1), one or more variants of the human cystein-rich intestinal protein 1 (CRIP1 variants), and proteolytic digestion products thereof in the sample; and comparing the amounts of the proteins to control amounts, which control amounts are determinative of the expression of the human epidermal growth factor receptor 2.

21 Claims, 12 Drawing Sheets
(7 of 12 Drawing Sheet(s) Filed in Color)

H&E m/z 4969          m/z 6225 m/z 4969          m/z 8404

IHC for HER2

H&E m/z 4969        m/z 6225

IHC for HER2

1 mm     H&E

HER2

DETERMINING AN EXPRESSION STATUS OF HUMAN EPIDERMAL GROWTH FACTOR RECEPTOR 2 (HER2) IN A BIOLOGICAL SAMPLE

PRIORITY INFORMATION

This patent application claims priority from U.S. provisional patent application Ser. No. 61/241,253 filed Sep. 10, 2009, which is hereby incorporated by reference.

BACKGROUND INFORMATION

The present invention relates to the field of cancer diagnosis and treatment and, in particular, to determining an expression status of human epidermal growth factor receptor 2 in a biological sample using mass spectrometry.

Adenocarcinoma of the breast is a leading cause of cancer morbidity and mortality among women worldwide. A major challenge faced by clinicians treating patients with breast cancer is how to best assess patient outcome and predict the clinical course of the disease so that the most appropriate treatment regimen can be identified. Determining the expression status of the human epidermal growth factor receptor 2 (HER2) in newly diagnosed breast cancer tissues is critically important for therapeutic decision making. Current guidelines recommend that the HER2 expression status should be evaluated for every patient with newly diagnosed, primary breast cancer.

Unlike most histopathologic testing, which serves as an adjunct to establishing a diagnosis, the results of HER2 testing stand alone in determining which patients afflicted with primary breast cancer are likely to respond to trastuzumab (Herceptin®), a monoclonal antibody directed to HER2. The HER2 expression status can be determined at the DNA-, the mRNA-, or the protein level. Various techniques are available for assessing these different target molecules, each with benefits and drawbacks. Although almost a decade has passed since trastuzumab was initially approved by the USA Food and Drug Administration (FDA), accurate HER2 expression status determination continues to challenge the field of clinical laboratory testing. Currently, two testing methods are approved by the FDA for HER2 testing of breast cancer tissues in the laboratory: immunohistochemical analysis (IHC) and fluorescence in situ hybridization (FISH). Studies using gene transcription profiles have shown that a gene related to human cystein-rich intestinal protein 1 (also referred to as CRIP1) in human breast cancers is similar to non-diseased tissues (Liu et al.: "*Thiamine Transporter Gene Expression and Exogenous Thiamine Modulate the Expression of Genes Involved in Drug and Prostaglandin Metabolism in Breast Cancer Cells*". Mol Cancer Res. 2004; 2:477-487; Ma et al.: "*Gene Expression Profiles of Human Breast Cancer Progression*". Proc Natl Acad Sci USA. 2003; 100:5974-5979) and other types of cancers. In experiments comparing transcription of the CRIP1 gene to matched normal breast tissue, the mRNA for the target was over-expressed 8 to 10-fold. Two recent studies compared differential gene transcription patterns in HER2-positive and HER2-negative breast cancer cell lines and tissues (Wilson et al.: "*Differential Gene Expression Patterns in HER2/Neu-Positive and -Negative Breast Cancer Cell Lines and Tissues*". Am J Pathol. 2002; 161(4):1171-85; Mackay et al.: "*cDNA Microarray Analysis of Genes Associated with ERBB2 (HER2/neu) Overexpression in Human Mammary Luminal Epithelial Cells*". Oncogene. 2003; 22(17):2680-8) wherein the mRNA of the CRIP1 gene and HER2-positive were both found to be up-regulated. In contrast to these genetic findings, an increased expression of the CRIP1 at the protein level has not yet been shown.

CRIP1 belongs to the LIM/double zinc finger protein family, which includes cysteine- and glycine-rich protein-1, rhombotin-1, rhombotin-2, and rhombotin-3. Human CRIP1, primarily a cytosolic protein, was cloned in 1997 using RT-PCR from human small intestine RNA and oligonucleotides whose sequence was derived from a human heart homologue of this protein, CRHP.

Mass spectrometry has been widely used to investigate protein patterns in biological samples, such as body fluids or homogenized tissues, to find biomarkers. Interrogation of the resulting complex mass spectrometry (MS) data sets using modern computational tools has provided identifications of both disease-state and patient-prognosis specific protein patterns. In general, biomarkers are used or at least predicted to be used for diagnosing cancer, qualifying different types of cancer, predicting a response to a cancer drug, and predicting a prognosis of a cancer patient. Biomarkers can further be measured and identified with high accuracy using tandem mass spectrometry with, for example, multiple reaction monitoring (MRM).

Matrix-assisted laser desorption/ionization (MALDI) imaging mass spectrometry (IMS) is a powerful tool for investigating protein patterns through direct, in situ, tissue section analyses. Similar to IHC and FISH, MALDI IMS has an advantage over other assay methods (e.g., methods utilizing homogenization) because MALDI IMS is morphologically driven. This allows the direct evaluation of tumor cells, correlation with other morphologic features and the ability to assay smaller patient tumor tissue specimens such as needle core biopsy specimens. MALDI IMS therefore is a seemingly ideal tool for rapid tissue diagnostics and molecular histology. In addition, MALDI IMS can also determine the distribution of hundreds of compounds in a single measurement without labeling.

Some studies have suggested that MALDI IMS provides accurate classifications (Yanagisawa et al.: "*Proteomic Patterns of Tumour Subsets in Non-Small-Cell Lung Cancer*", The Lancet, Volume 362, Issue 9382, 9 Aug. 2003, Pages 433-439; Schwartz et al.: "*Proteomic-Based Prognosis of Brain Tumor Patients Using Direct-Tissue Matrix-Assisted Laser Desorption Ionization Mass Spectrometry*". Cancer Res. 2005 Sep. 1; 65(17):7674-81). MALDI IMS has been applied to various types of diseased tissues, including human non-small cell lung tumors, gliomas, as well as ovarian and breast cancers. From recent publications it has also become clear that the integration of MALDI IMS into clinical management regarding disease diagnosis and outcome prediction will likely occur in the near future. (Franck et al.: "*MALDI IMAGING: State of the Art Technology in Clinical Proteomics*". Mol Cell Proteomics. 2009 May 18; Cornett et al.: "*MALDI Imaging Mass Spectrometry: Molecular Snapshots of Biochemical Systems*". Nat Methods. 2007; 4(10):828-33). As MALDI IMS protein expression data becomes available for various tumor tissue types, this approach will provide a common disease-wide methodology that can be applied to a variety of clinical situations. While many of the MALDI IMS studies focus on the identification of new biomarkers, so far only a few studies have evaluated the potential of MALDI IMS for molecular classification of tissues based on protein patterns.

SUMMARY OF THE INVENTION

According to a first aspect of the invention, a method is provided for determining an expression of human epidermal growth factor receptor 2 (HER2) of a subject. The method includes providing a sample from the subject (e.g., a human patient with breast cancer); measuring one of (i) amounts of two or more proteins in the sample, each protein having a molecular weight substantially equal to 4740, 8404, 8419, 8435, 8450, 8455, 8465, 8570, 8607 or 8626 atomic mass units, and (ii) amounts of at least one of human cystein-rich intestinal protein 1 (CRIP1), one or more variants of the human cystein-rich intestinal protein 1 (CRIP1 variants), and proteolytic digestion products thereof in the sample; and comparing the amounts of the proteins to control amounts, where the control amounts are determinative of the expression of the human epidermal growth factor receptor 2.

According to a second aspect of the invention, a method is provided for predicting a response of a cancer patient to a drug and/or predicting a prognosis of a cancer patient. The method includes providing a sample from the patient; measuring amounts of at least one of the human cystein-rich intestinal protein 1 (CRIP1), one or more variants of the Cystein-rich intestinal protein 1 (CRIP1 variants), and proteolytic digestion products thereof in the sample; and comparing the amounts of the variants to control amounts. The control amounts are deter mined from samples of (i) patients responding or not responding to the drug, or (ii) patients with different prognosis.

According to a third aspect of the invention, a method is provided for diagnosing cancer in a subject. The method includes the steps of providing a liquid sample from the subject selected from the group comprising serum, plasma, whole blood, nipple aspirate fluid, cerebrospinal fluid and urine; measuring the amounts of at least one of the human cystein-rich intestinal protein 1 (CRIP1), one or more variants of the Cystein-rich intestinal protein 1 (CRIP1 variants), and proteolytic digestion products thereof in the sample; and comparing the amounts of the variants to control amounts, where the control amounts are determined from samples of healthy subjects.

According to a fourth aspect of the invention, a kit is provided for determining an expression status of human epidermal growth factor receptor 2 (HER2), diagnosing cancer, predicting a patient response to a drug, and/or predicting a prognosis of a cancer patient. The kit includes an antibody or other affinity reagents. The antibody or other affinity reagents include aptamers or affibodies, which are specific for human cystein-rich intestinal protein 1 or its variants.

These and other objects, features and advantages of the present invention will become more apparent in light of the following detailed description of preferred embodiments thereof, as illustrated in the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
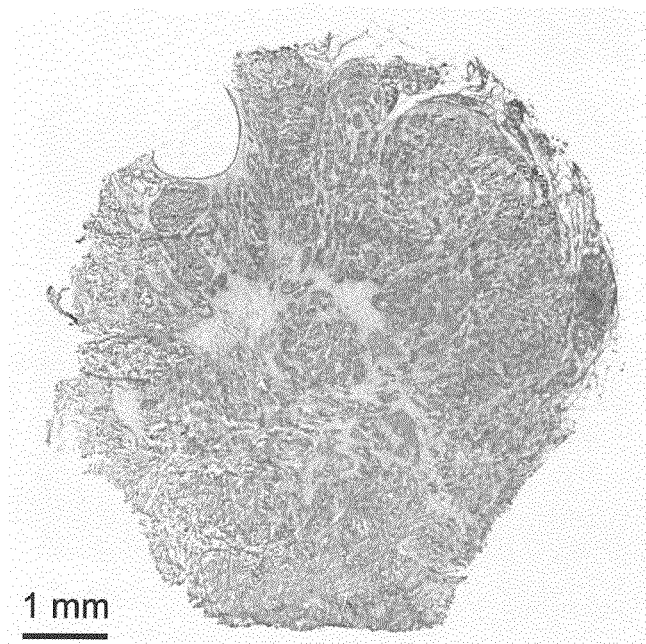
FIG. 1 is a MALDI IMS microscopic image of a HER2-positive breast cancer tissue section stained with H&E.

Clinicians typically assess patient outcomes and predict clinical courses of a disease in order to identify appropriate cancer treatment regimes. Current guidelines, for example, recommend that clinicians determine an expression status (or "expression") of human epidermal growth factor receptor 2 (HER2) for each new patient diagnosed with primary breast cancer. The following describes a study performed by the inventors for determining the HER2 expression status by analyzing tissue sections using, for example, Matrix-Assisted Laser Desorption/Ionization Imaging Mass Spectrometry (MALDI-IMS) technology.

SAMPLE COLLECTION AND TUMOR TISSUE SPECIMENS: Forty eight (48) primary breast cancer patients presenting with invasive ductal carcinoma participated in this study. Thirty (30) of the patients participated in a discovery set, and eighteen (18) of the patients participated in a validation set. Each patient provided informed written consent, and the study was approved by Ethics Committee of the Technische Universität München. The patients underwent primary surgical resection at the Department of Obstetrics and Gynecology, Klinikum rechts der Isar, Technische Universität München. Tumor tissue samples removed from each of the patients were snap-frozen and stored in liquid nitrogen in a tissue bank at the Institute of Pathology, Technische Universität München. Histomorphological and clinical characteristics of each analyzed case are listed below in Table 1.

ASSESSMENT OF HER2 EXPRESSION STATUS: Each case was carefully reviewed before being included in the study for the HER2 expression status. The discovery set was evaluated by immunohistochemistry ("IHC") and fluorescence in situ hybridization ("FISH"), and the validation set was evaluated by IHC. Scoring criteria were applied according to the American Society of Clinical Oncology/College of American Pathologists guideline recommendations for HER2 testing in breast cancer. A positive HER2 result is indicated, for example, by an IHC staining of 3+ (uniform, intense membrane staining of more than 30% of invasive tumor cells), a FISH result of more than six HER2 gene copies per nucleus or a FISH ratio (HER2 gene signals to chromosome 17 signals) of more than 2.2. A negative HER2 result is indicated by an IHC staining of 0 or 1+, a FISH result of less than 4.0 HER2 gene copies per nucleus or FISH ratio of less than 1.8. In total, forty eight frozen tissue samples from patients with invasive ductal breast cancer were used and the pre-characterized HER2 expression status was reconfirmed for each sample by IHC on a consecutive cryosection.

MALDI IMAGING MASS SPECTROMETRY (MALDI IMS) EXPERIMENTS: The samples were cryosectioned on conductive Indium-Tin-Oxide ("ITO") coated glass slides, briefly washed in 70% and 100% ethanol, dried under vacuum, and covered with a matrix. The MALDI matrix was applied using an ImagePrep station (Bruker Daltonik GmbH, Bremen, Germany) and a standard protocol provided with the instrument. Sinapinic acid (Sigma-Aldrich, Taufkirchen, Germany) at 10 mg/ml in water/acetonitrile 40:60 (v/v) with 0.2% trifluoroacetic acid (TFA, Applied Biosystems, Darmstadt, Germany) was used as the matrix for the MALDI measurements. The MALDI measurements were performed on an Ultraflex III MALDI-TOF/TOF in linear mode with a mass range of 2400-25000 atomic mass units ("u") with a sampling rate of 0.1 GS/s using FlexControl 3.0 and FlexImaging 2.1 software packages (all Bruker Daltonik GmbH, Bremen, Germany). The lateral resolution for the MALDI IMS was set to 200 µm and a total of 200 laser shots were accumulated per pixel at a substantially constant laser power.

Following the MALDI IMS experiments, the cryosections were incubated in 70% ethanol to remove the matrix and then washed in distilled water. The same section that was measured by the MALDI IMS was also stained with hematoxylin and eosin (H&E), scanned with a MIRAX® DESK system (Carl Zeiss MicroImaging GmbH, Göttingen, Germany), and co-registered with the MALDI IMS results to correlate mass spectrometric data with the histological features of the section.

STATISTICAL ANALYSIS: Tumor associated spectra were selected using the FlexImaging 2.1 software. Each tissue section region of interest ("ROI") that contained invasive ductal breast cancer tissue specific for HER2-positive and HER2-negative cell populations was identified. The extracted mass spectra, which included approximately 300 peaks per spectrum, underwent recalibration on common "background" peaks (also known as "spectral alignment") and normalization based on their total ion count in the observation mass range using ClinProTools 2.2 software (Bruker Daltonik GmbH, Bremen, Germany). An average spectrum across each of the spectra of a ROI was used for peak defining integration ranges. The integration ranges were used to obtain the average peak intensities of each respective ROI. Significant differences in peak intensities between both histological groups (HER2-positive and HER2-negative) were evaluated by the Wilcoxon rank-sum test with a significance cutoff point of $p<0.05$.

Data was exported to the R statistical software (R Foundation for Statistical Computing) to compare the quality of two different classification algorithms predicting HER2 expression status. The samples in the discovery set were processed on a support vector machine (SVM) and an artificial neuronal network (ANN). Both classifiers were respectively tested internally and externally using a 10-fold cross validation and the validation set. At each evaluation step, features were selected that best segregated the samples within the training set into the related groups (i.e., HER2-positive or HER2-negative), where an MS signal was included once its area under curve (AUC) exceeded 0.8 as calculated by receiver operating characteristics (ROC) analysis. The performances of both approaches were then compared by analyzing the resulting confusion matrices across each of the evaluation steps.

The additional hierarchical clustering of the expression profiles of each of the samples was carried out with the software CLUTO (George Karypis, Department of Computer Science & Engineering, University of Minnesota, USA) on the standardized, exported data. CLUTO is a software package for clustering low- and high-dimensional datasets and for analyzing the characteristics of the various clusters.

RESULTS: Thirty tumor tissue samples, 15 HER2-negative samples and 15 HER2-positive samples, were analyzed in the initial discovery set. 1129 individual mass spectra, representing specific HER2-positive or HER2-negative tumor cell populations defined by ROIs, were used for comparative analyses. The results of the comparative analysis are exemplified in FIGS. 1 to 16.

Figure 2:
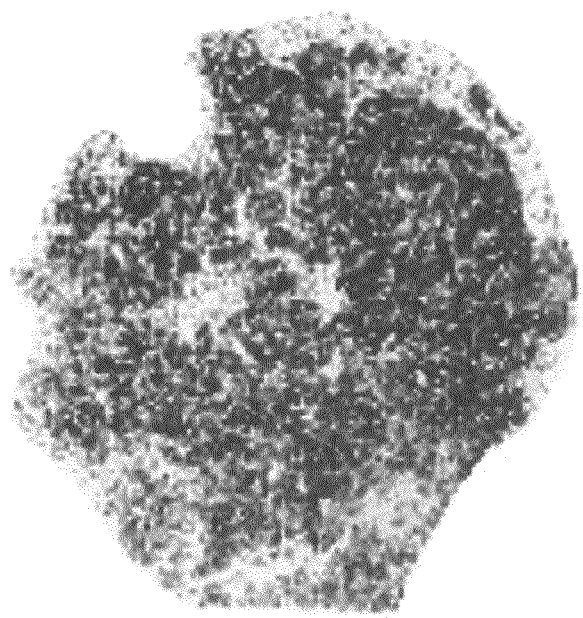
FIG. 2 is an ion density image of protein markers m/z 4969 and 6225 in the HER2-positive breast cancer tissue section in FIG. 1, where both the m/z 4969 and 6225 markers are visible.
Figure 3:
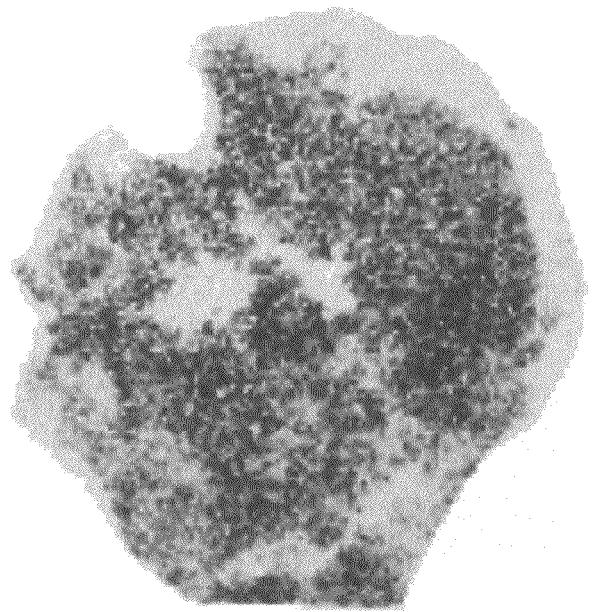
FIG. 3 is an ion density image of protein markers m/z 4969 and 8404 in the HER2-positive breast cancer tissue section in FIG. 1, where both the m/z 4969 and 8404 markers are visible.
Figure 4:
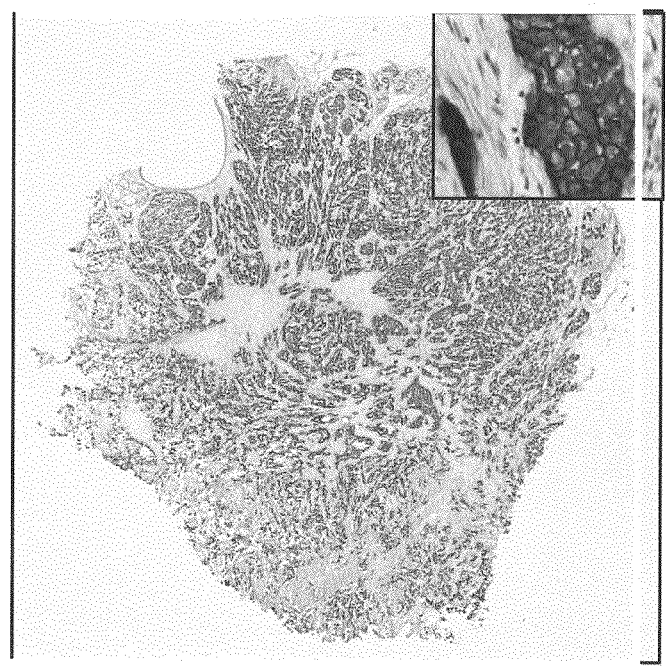
FIG. 4 is a MALDI IMS microscopic image of a serial HER2-positive breast cancer tissue section that has been classified with a score of 3+ using immunohistochemistry for HER2.
Figure 5:
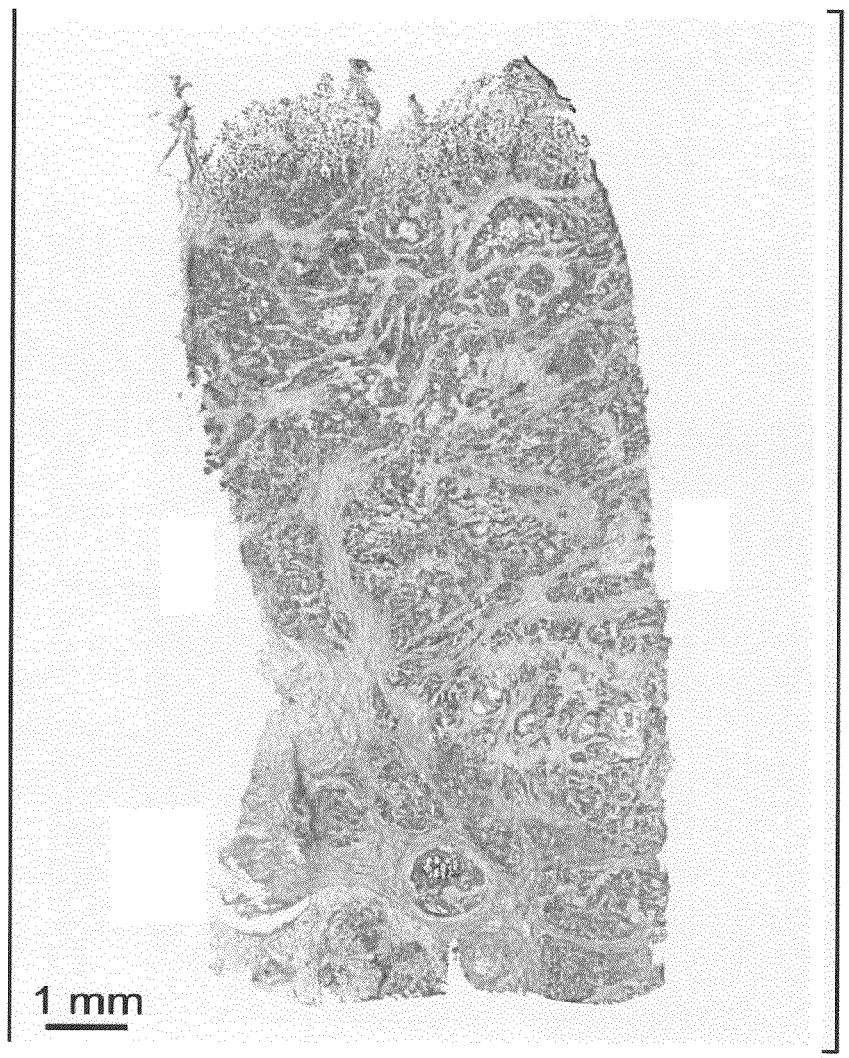
FIG. 5 is a MALDI IMS microscopic image of a HER2-negative breast cancer tissue section stained with H&E.
Figure 6:
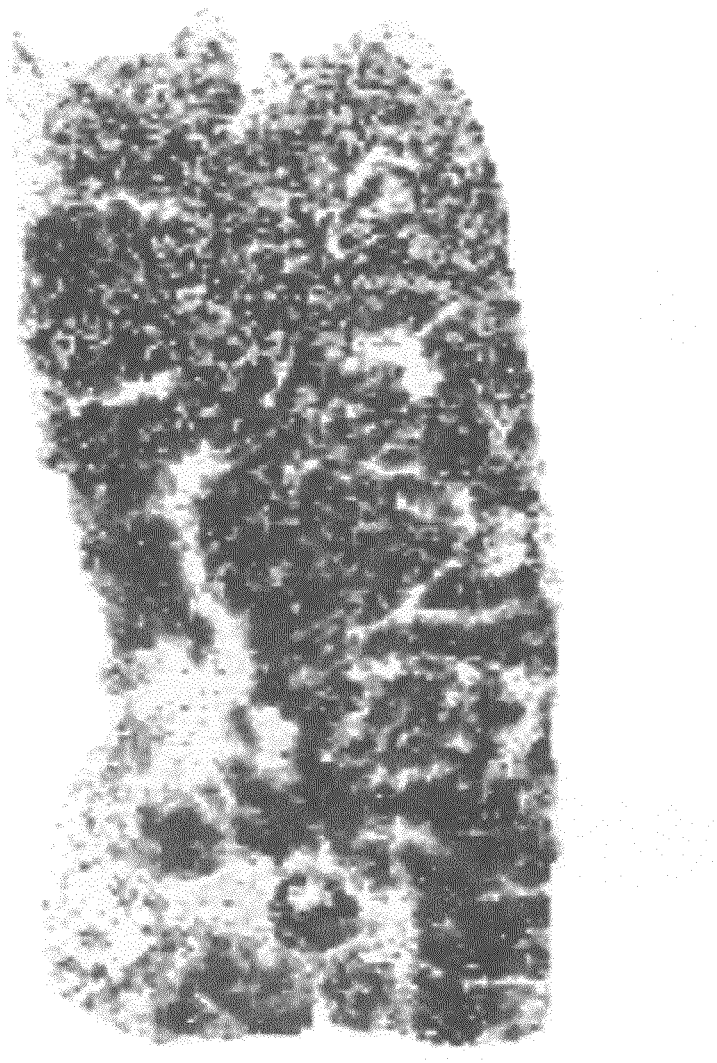
FIG. 6 is an ion density image of protein markers m/z 4969 and 6225 in the HER2-negative breast cancer tissue section in FIG. 5, where both the m/z 4969 and 6225 markers are visible and, therefore, do not distinguish between HER2-positive and negative samples.
Figure 7:
FIG. 7 is an ion density image of protein markers m/z 4969 and 8404 in the HER2-negative breast cancer tissue section in FIG. 5, where the m/z 8404 marker is not visible and, therefore, distinguishes between HER2-positive and negative samples.
Figure 8:
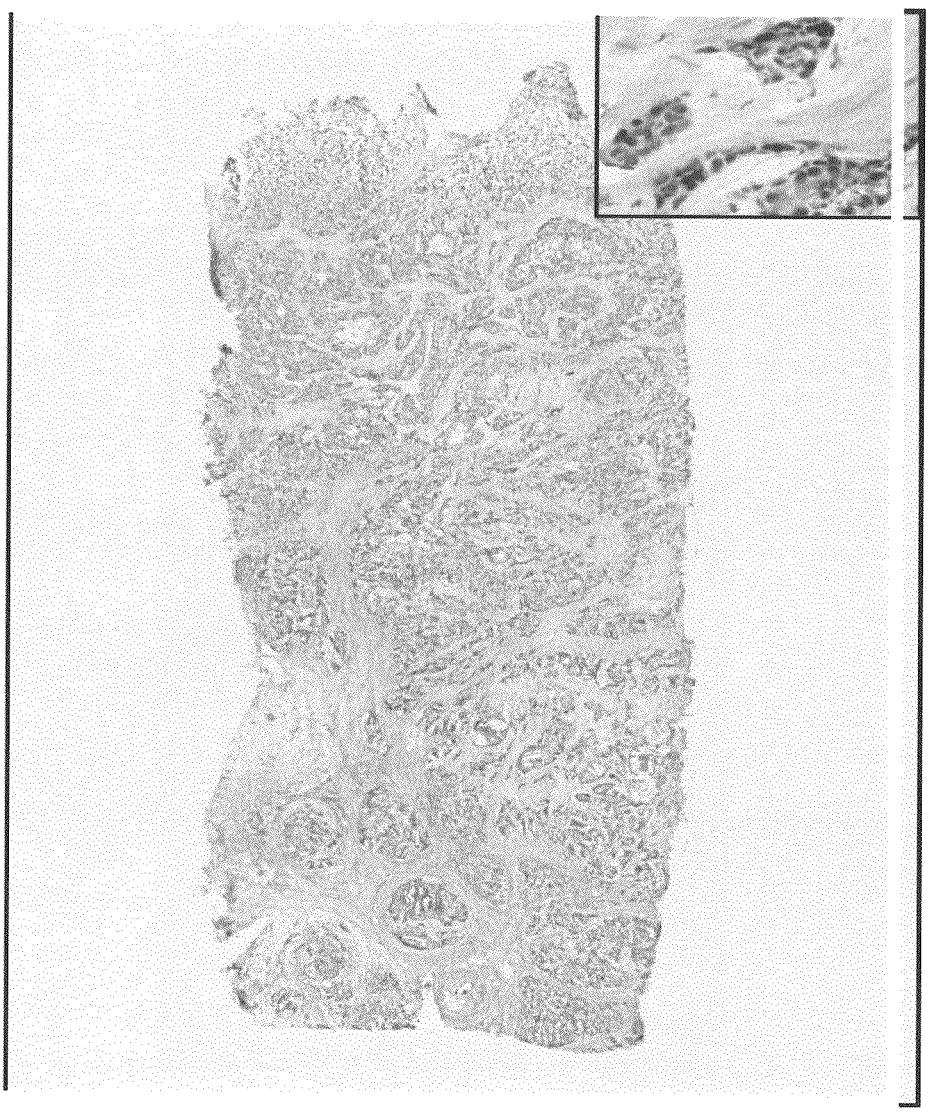
FIG. 8 is a MALDI IMS microscopic image of a serial HER2-negative breast cancer tissue section that has been classified with a score of 0 using immunohistochemistry for HER2.
Figure 9:
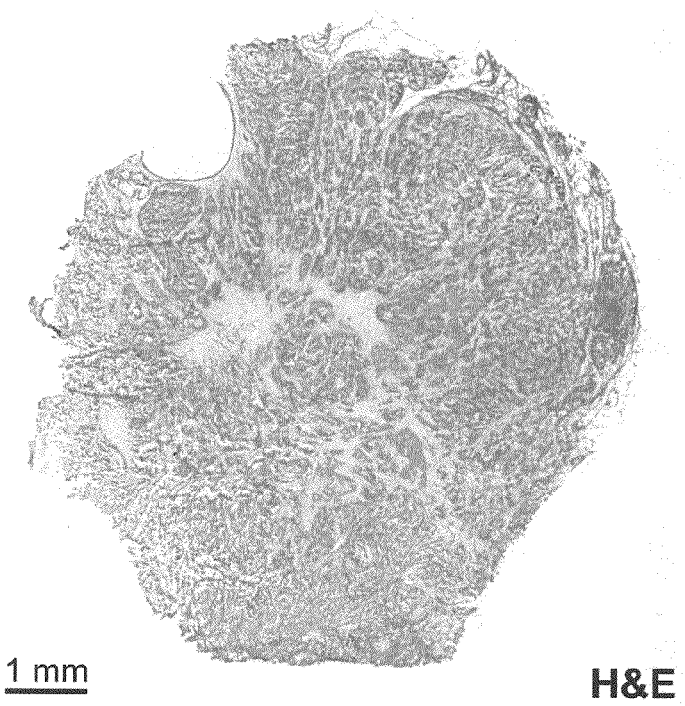
FIG. 9 is a MALDI IMS microscopic image of a HER2-positive breast cancer tissue section stained with hematoxylin and eosin ("H&E")
Figure 10:
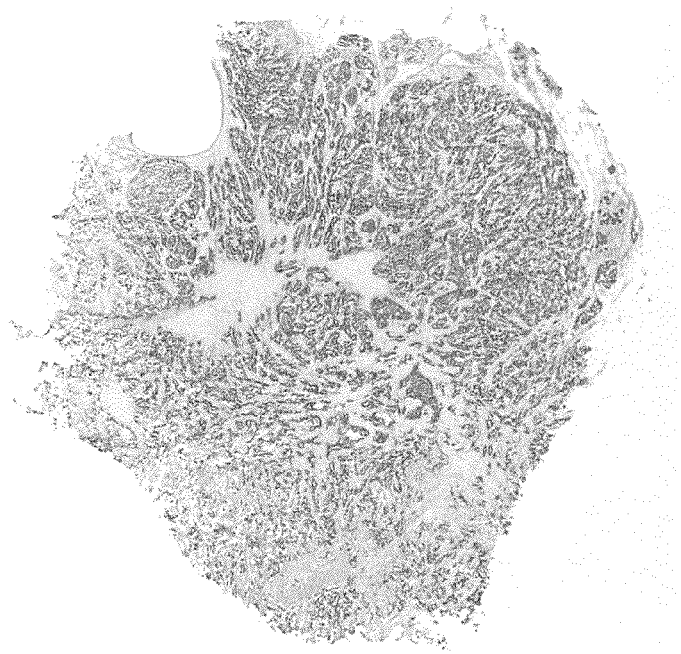
FIG. 10 is a MALDI IMS microscopic image of a serial HER2-positive breast cancer tissue section that has been classified with a score of 3+ using immunohistochemistry for HER2.
Figure 11:
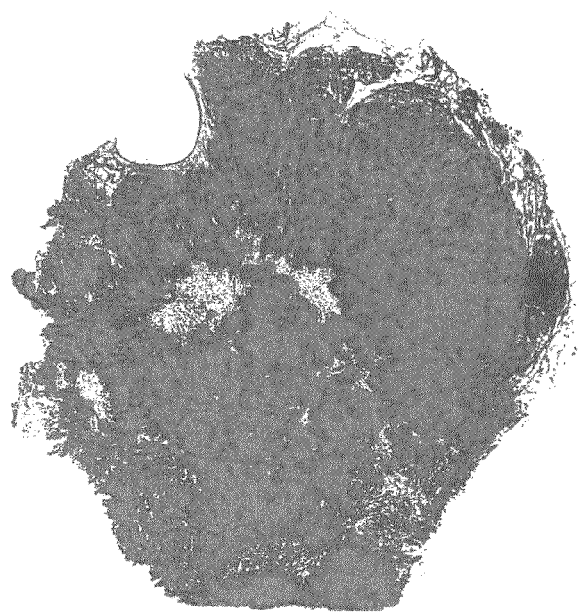
FIG. 11 is an ion density image of a protein marker, having an atomic weight of 8419 m/z, in the HER2-positive breast cancer tissue section in FIG. 2A, which is overlaid on the image in FIG. 2A.
Figure 12:
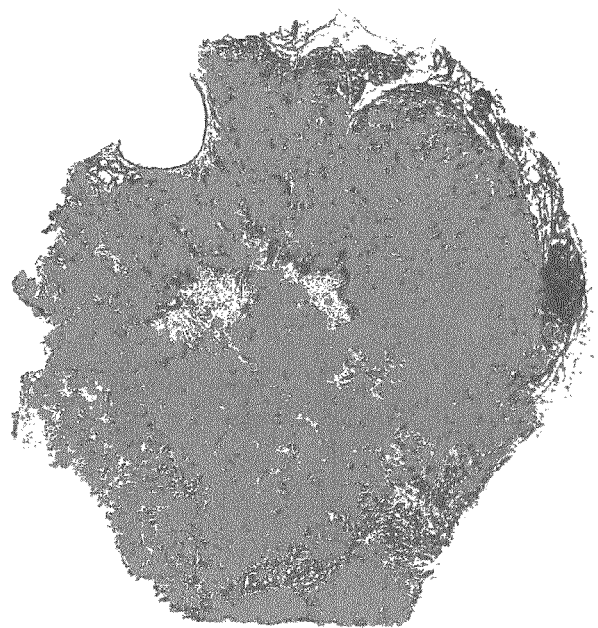
FIG. 12 is an ion density image of another protein marker, having an atomic weight of 8455 m/z, in the HER2-positive breast cancer tissue section in FIG. 9, which is overlaid on the image in FIG. 9.
Figure 13:
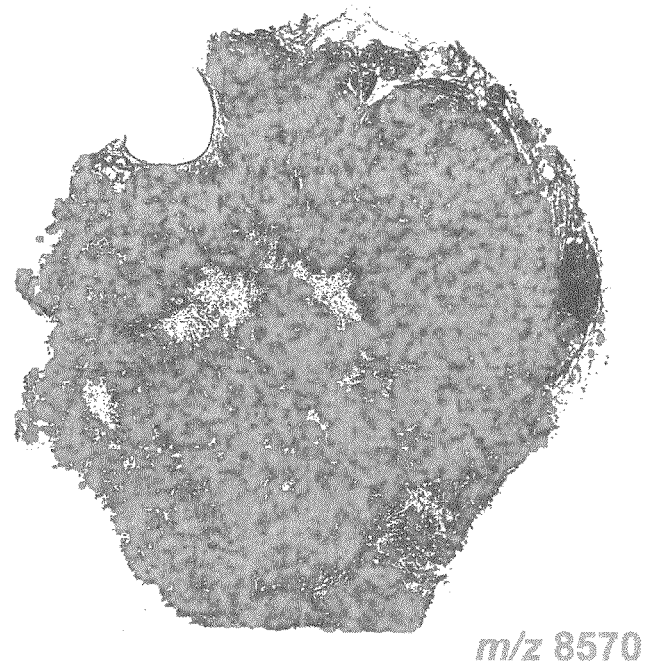
FIG. 13 is an ion density image of another protein marker, having an atomic weight of 8570 m/z, in the HER2-positive breast cancer tissue section in FIG. 2A, which is overlaid on the image in FIG. 9.
Figure 14:
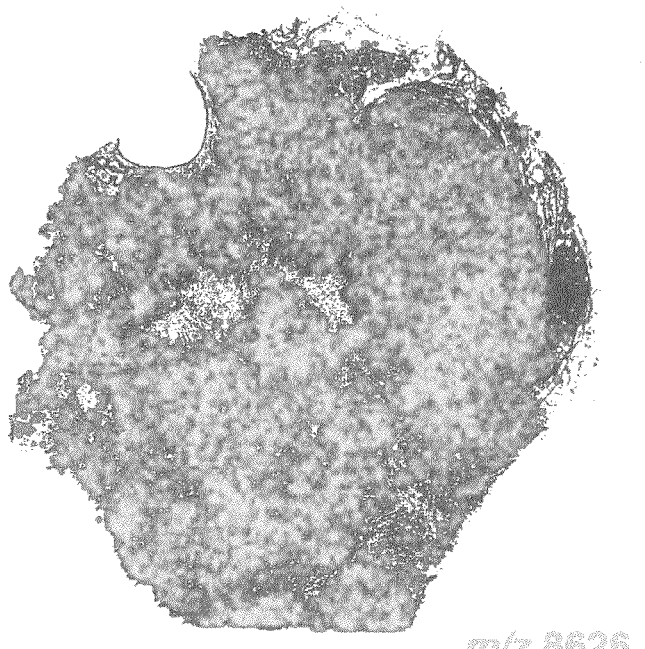
FIG. 14 is an ion density image of another protein marker, having an atomic weight of 8626 m/z, in the HER2-positive breast cancer tissue section in FIG. 2A, which is overlaid on the image in FIG. 9.
Figure 15:
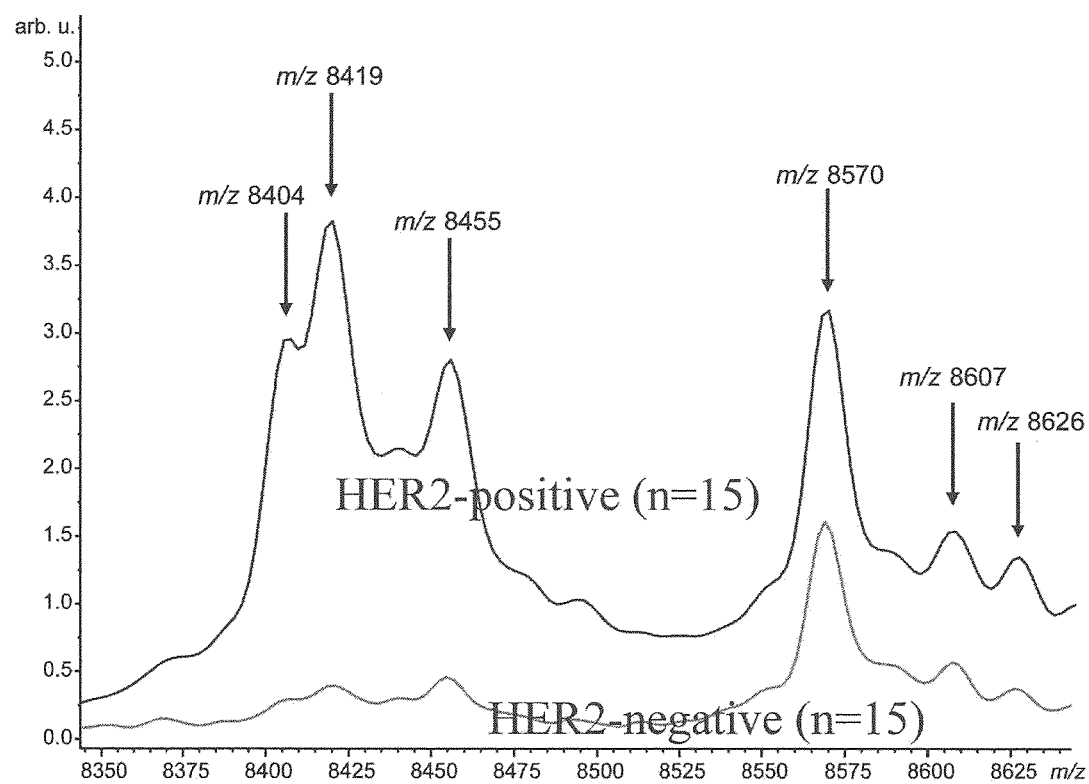
FIG. 15 is a graphic illustration of averaged MALDI-TOF MS spectra for HER2-positive (n=15) and HER2-negative (n=15) breast cancer tissues, from a discovery set, in a mass range of m/z 8345 to 8640, where the arrows mark six peaks with significant differences between the HER2-positive and HER2-negative groups with centroid masses at m/z 8404, 8419, 8455, 8570, 8607, and 8626.

FIGS. 2, 3, 6 and 7 illustrate various species specific peaks in tumor stroma tissue samples. FIGS. 2 and 3 illustrate a tissue sample with a strong immunoreactivity score of 3+ that is HER2-positive, while FIGS. 6 and 7 illustrate a tissue sample with a immunoreactivity score of 0 that is HER2-negative. Referring still to FIGS. 2, 3, 6 and 7, a peak at m/z 4969 is shown having little or no expression in cancer cells. Referring to FIGS. 2 and 6, a peak at m/z 6225 is shown that expresses in both HER2-positive and HER2-negative cancer cells. The peak at m/z 6225, therefore, does not distinguish between the HER2-positive and the HER2-negative tumor cells. Referring to FIGS. 3 and 7, a peak at m/z 8404 is shown that is highly up-regulated in the HER2-positive tissue sample (see FIG. 3), but absent in HER2-negative tissue sample (see FIG. 7). The peak at m/z 8404, therefore, can be used to distinguish between the HER2-positive and the HER2-negative tumor cells.

Referring to FIGS. 11-15, five peptide ions in the mass range m/z 8345 to 8640 are shown having an over-expression in HER2-positive samples as compared to the HER2-negative sample. During the study, seven m/z species were found at an average of m/z 4740, m/z 8404, m/z 8419, m/z 8455, m/z 8570, in/z 8607 and m/z 8626 that can discriminate between HER2-positive and HER2-negative tumor samples (see FIG. 16). The peaks were clearly different from background noise and were determined with a mass accuracy of ±4 u average molecular weight in linear mode. In addition to the above referenced MS signals shown in the FIGS. 1 to 16, an additional differentiating MS signal exists at about m/z 22490 for invasive ductal cancer cells. The peak at m/z 22490, however, is not present in tumor stroma or other tissue components.

Figure 16:
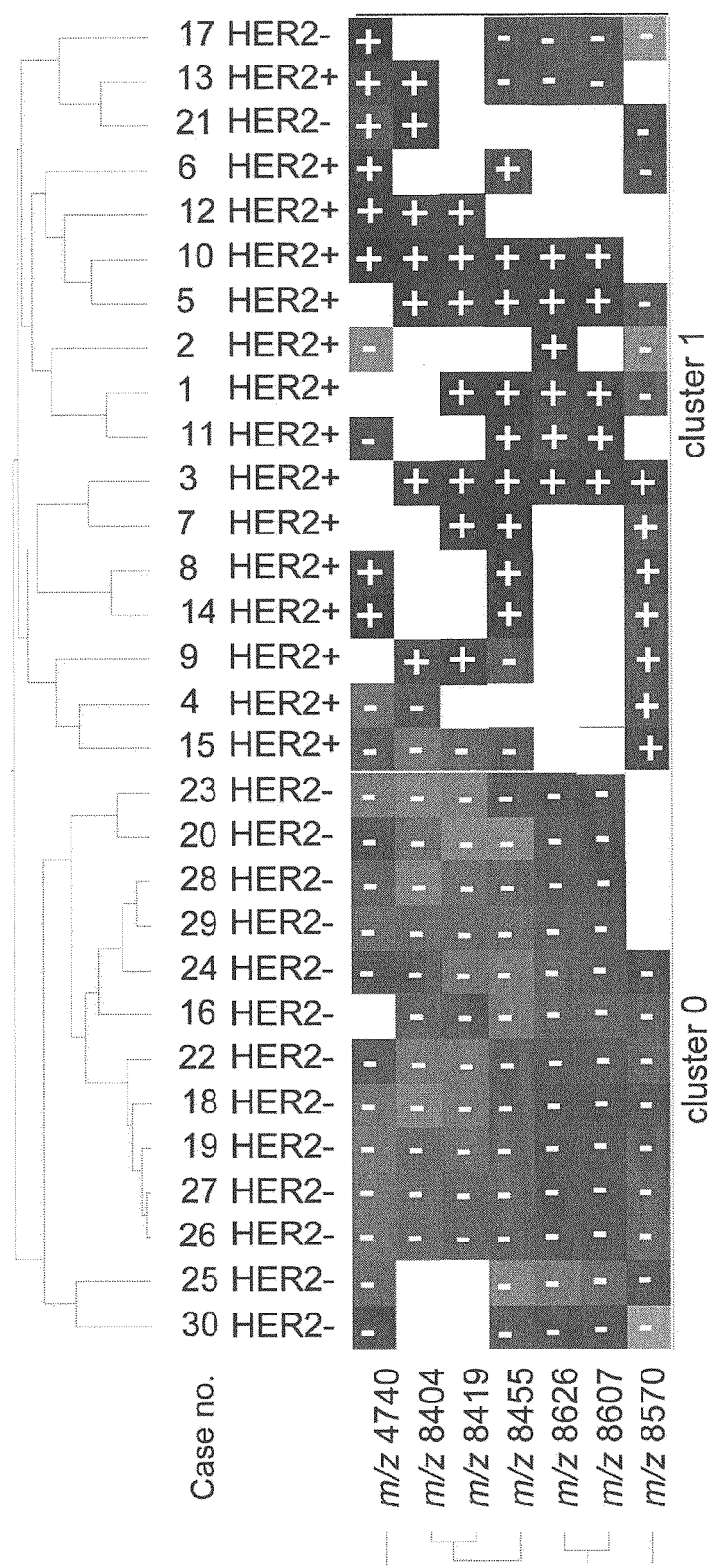
FIG. 16 is a hierarchical clustering of breast cancer tumor tissue specimens from the discovery set, where the samples were respectively clustered according to the expression pattern of the seven discriminating peptide ions at m/z 4740, 8404, 8419, 8455, 8570, 8607, and 8626.

Referring to FIG. 16, a hierarchical clustering is shown of breast cancer tumor tissue specimens from the discovery set. The samples were respectively clustered according to their expression pattern of the seven discriminating peptide ions at m/z 4740, 8404, 8419, 8455, 8570, 8607, and 8626. Peak intensities were standardized before clustering. Over-expressed peptide signals are shown as plus signs, under-expressed peptide signals are shown as minus signs, and unchanged peptide signals are shown as blank. The algorithm identified two clusters (shown as cluster 0 and cluster 1). While one cluster harbors HER2-negative samples (n=13), two HER2-negative samples (case numbers 17 and 21) were assigned as false-positives to the HER2-positive designated group.

A 10-fold cross-validation was applied on the sample data (discovery set) to assess the performance of the classifiers SVM and ANN. The ANN outperformed the SVM with a correct classification rate of 90% and, therefore, provides reliable discrimination between HER2-positive and HER2-negative groups. The classification ability of both classifiers (SVM and ANN) was also used to predict the HER2 expression status of the tissues from the validation set (n=18). The predictions resulted in a misclassification of two cases. Both the ANN and the SVM approaches therefore achieved an overall accuracy of approximately 89%, with a sensitivity of approximately 83% and a specificity of approximately 92% (see Table 1 below).

TABLE 1

Clinical and Molecular Characteristics of the Patient Series

| Set Characteristics | Discovery Set | Validation Set |
|---|---|---|
| Patients | 30 | 18 |
| Mean age (range) | 60.1 (38-91) | 61.4 (36-84) |
| HER2 expression status | | |
| IHC | | |
| Score 3+ | 13 | 6 |
| Score 2+ | 2 | 0 |
| Score 1+ | 2 | 6 |
| Score 0 | 13 | 6 |
| FISH | | |
| positive | 15 | n.a. |
| negative | 15 | n.a. |
| pT classification | | |
| pT1mic | 0 | 1 |
| pT1a | 2 | 0 |
| pT1b | 1 | 0 |
| pT1c | 9 | 0 |
| pT2 | 16 | 11 |
| pT3 | 1 | 1 |
| pT4 | 1 | 0 |
| pTx | 0 | 5 |
| pN classification | | |
| positive | 17 | 6 |
| negative | 12 | 7 |
| pNx | 1 | 5 |
| Grading | | |
| Grade 1 | 0 | 0 |
| Grade 2 | 3 | 6 |
| Grade 3 | 27 | 12 |
| ER/PR status | | |
| ER+ | 14 | 5 |
| ER− | 16 | 13 |
| PR+ | 9 | 13 |
| PR− | 21 | 5 |

| Proteomic classification | Discovery set* | Validation set |
|---|---|---|
| Support Vector Machine | | |
| Accuracy | 87% | 89% |
| | (95% CI 70%-96%) | (95% CI 65%-99%) |
| Sensitivity | 87% | 83% |
| Specificity | 87% | 92% |
| Artificial Neuronal Network | | |
| Accuracy | 90% | 89% |
| | (95% CI 73%-98%) | (95% CI 65%-99%) |
| Sensitivity | 87% | 83% |
| Specificity | 93% | 92% |

Table Key:
HER2 = human epidermal growth factor receptor 2,
IHC = immunohistochemistry,
FISH = fluorescence in situ hybridization,
ER = estrogen receptor,
PR = progesterone receptor,
CI = confidence interval,
n.a. = not analyzed
*Classifiers were evaluated using a 10-fold cross-validation IDENTIFICATION OF A MARKER PROTEIN BY TISSUE LYSIS AND TANDEM MASS SPECTROMETRIC ANALYSIS: Two human HER2-positive breast cancer biopsy slices (10 μm thickness, not previously stained or analyzed by MALDI imaging) were placed in a 1.5 ml Eppendorf tube with 50 μl 0.1% TFA followed by a 2 min centrifugation (20,000 g) to spin down the tissue (Eppendorf Centrifuge 5804 R, Eppendorf, Germany) Ultrasonication in an ice bath was applied for 30 minutes to lyse the tissue. Centrifugation (20,000 g) was performed at 4° C. for 30 minutes. Tissue lysate was further processed with ultrafiltration (Vivaspin 500, cutoff 5 ku, Sartorius Stedim Biotech, France). Twenty-five (25) μl of supernatant from centrifugation was pipetted into a spin column and centrifuged for one hour at 15,000 g. Twenty-five (25) μl 0.1% TFA was added to the spin column and centrifuged again for one hour to wash the lysate. The spin column was refilled to 25 μl (0.1% TFA), the membrane was rinsed with the solution to obtain proteins, and the solution was transferred into an auto sampler vial. Intact proteins were then separated with an Agilent mRP column (5 μm, 0.5×100 mm) and Agilent 1200 HPLC system (Agilent Technologies, Böblingen, Germany). During the separation, the following LC parameters were used: flow rate of 12 μl/min, column oven set to 60° C., injection volume of 8 solvent A 0.1% formic acid (Sigma-Aldrich) in water, solvent B 0.1% formic acid in acetonitrile (ACN, Sigma-Aldrich), step wise gradient 7 minutes at 3% B, in 23 minutes to 22% B, in 5 minutes to 38% B, in 2 minutes to 97% B, 5 minutes at 97% B, in 2 minutes to 3% B, and 5 minutes at 3% B. Fractionation was performed with a Proteineer fc (Bruker Daltonik GmbH, Bremen, Germany) from 10-42 minutes with 20 second time slices into a 96 well plate, and two separations were collected in a well plate. For candidate localization 0.5 µl from collected fractions were spotted onto 96PAC target and analyzed with an Ultraflex III MALDI-TOF/TOF in linear mode (both: Bruker Daltonik GmbH, Bremen, Germany).

Three subsequent fractions including the candidate peptides were combined (approximately 15 µl) and diluted with 1.5 µl 2-propanol (Sigma-Aldrich) and 7.5 µl ACN/H$_2$O with 0.2% formic acid for ETD/PTR fragmentation. Infusion MS experiments were performed with TriVersa NanoMate (10 µl sample, 384 well plate, D-chip with 0.4 psi and 1.55 kV; Advion Biosystems, Ithaca, N.Y., USA) and amazon ETD Ion Trap (Bruker Daltonik GmbH, Bremen, Germany). Briefly, the sample was measured with a Maximum Scan Mode at 4600/sec, positive polarity, a Scan Range from m/z 100-3000, an average of ten spectra and a rolling average of four. A precursor was chosen of m/z 602.4 (charge state 14$^+$) with an analyte ICC of 125,000 and an isolation width of m/z 4.0, MS$^2$ stage was ETD with reaction time of 45 ms and reactant ICC of 115,000, MS$^3$ stage was PTR with reaction time of 80 ms and reactant ICC of 175,000. Acquired ETD/PTR spectra were processed using DataAnalysis 4.0 with the SNAPII algorithm, and deconvoluted spectra were further analyzed with BioTools 3.2 (all Bruker Daltonik GmbH, Bremen, Germany) and submitted to a Mascot (Matrix Science, London, UK) database search (Mascot 2.2.04, SwissProt 56.1, taxonomy: mammals, Peptide mass tolerance+/−10 u, fragment mass tolerance+/−0.8 u, Instrument type ETD-Trap). The identified protein sequence was manually validated in BioTools on a residue-by residue basis using the raw data.

Cystein-rich protein 1 ("CRIP1_HUMAN") was identified by performing a database search with a mascot score of 126. A theoretical average molecular weight of 8402 u was calculated from an underivatized CRIP1_HUMAN des-Met 1 gene sequence which was in good agreement with the MALDI and ESI data. A cluster of CRIP1 variants at 8419, 8435, 8450 and 8464 u were determined experimentally, however, after charge deconvolution of the multiple charge states in the ion trap ESI spectrum. The varying molecular weights are caused by one or more structural variations, wherein the human cystein-rich intestinal protein 1 is modified; e.g., by disulfide bond formation and/or one or more methyl groups and/or oxygen atoms and/or by at least one mutation.

The MALDI IMS proteomic method described above is a label-free and morphology-driven alternative to HER2 testing in breast cancer tissues. The method, however, may also be used for testing other cancer diseases besides breast cancer. Advantageously, this method may be performed using small amounts of fresh-frozen and unprocessed tumor tissue, which are typically available in a clinical setting, to obtain the profiles of the marker proteins that can be used to accurately classify tumors associated with molecular features such as HER2. The tissue sample may be obtained using core needle biopsies or can be available as a tissue microarray set.

Beyond classification of HER2 expression status, some of the differentially expressed species may be, directly or indirectly, responsible for the more aggressive properties of HER2 over-expressing cancer cells. In addition to defining new diagnostic and prognostic markers, the aforedescribed method may also provide new therapeutic targets and can be used to allocate patients with small tumors to good or poor prognostic groups, and to predict response to endocrine therapy (e.g. tamoxifen or aromatase inhibitors) or to immunotherapy with trastuzumab.

According to an aspect of the invention a method is provided for determining an expression status of the human epidermal growth factor receptor 2 (HER2) of a subject. The method includes (a) providing a sample from the subject, (b) measuring amounts of two or more marker proteins in the sample, wherein the two or more marker proteins have substantially one of following molecular weights 4740, 8404, 8419, 8455, 8570, 8607 or 8626 atomic mass units, and (c) comparing the amounts of the marker proteins to control amounts determinative of the expression of the human epidermal growth factor receptor 2.

The expression of the human epidermal growth factor receptor 2 is determined as up-regulated when, for example, amounts of the marker proteins are increased compared to the control amounts, especially in breast tissue. To improve the determination of the expression status, therefore, three or more of the marker proteins may be measured in step (b). In other embodiments, each of the seven marker proteins may be measured in step (b).

The proteins having molecular weights of 4740, 8455, 8570, 8607 and 8626 atomic mass units are presumably related to fragments of higher molecular weight proteins correlated with HER2, whereas the marker proteins having molecular weights of 8404 and 8419 atomic mass units are respectively related, within normal mass accuracy, to the human cystein-rich intestinal protein 1 (CRIP1) and a variant thereof. The underivatized CRIP1_HUMAN des-Met 1 has an average molecular weight of 8402 u calculated based on the gene sequence. The modified molecular weight of the variant can be a result of a modification, a post-translational modification, a sequence variation and/or a sequence length variation.

According to aspect of the invention, a method is provided for determining the expression status of the human epidermal growth factor receptor 2 (HER2) of a subject. The method includes (a) providing a sample from the subject (see step 400 in FIG. 17), (b) measuring amounts of human cystein-rich intestinal protein 1 (CRIP1), one or more variants of the human cystein-rich intestinal protein 1, and/or proteolytic digestion products thereof in the sample (see step 402 in FIG. 17), and (c) comparing the amounts of the variants to control amounts determinative of the expression of the human epidermal growth factor receptor 2 (see step 404 in FIG. 17).

The variants of the human cystein-rich intestinal protein 1 (CRIP1 variants) may have one of following molecular weights 8419, 8435, 8450 or 8465 atomic mass units. These and other variations can result from one or more structural variations, wherein the human cystein-rich intestinal protein 1 is modified. The human cystein-rich intestinal protein 1 can be modified, for example, by disulfide bond formation and/or one or more methyl groups and/or oxygen atoms and/or by at least one mutation.

Figure 17:
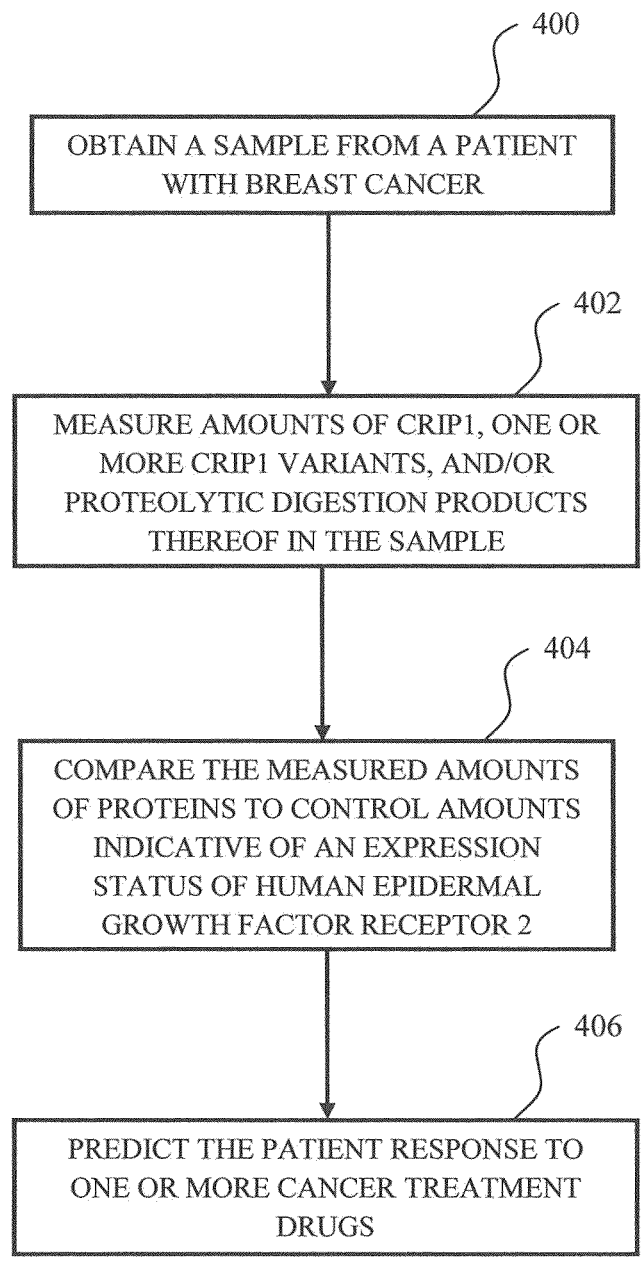
FIG. 17 is an illustration of a method for predicting a patient response to one or more cancer treatment drugs.

Referring to step 402 in FIG. 17, the expression of the human epidermal growth factor receptor 2 is determined as up-regulated when, for example, amounts of CRIP1 and/or CRIP1 variants are increased compared to the control amounts, especially where the sample is from breast tissue.

The HER2 oncogene encodes a 185 ku epidermal growth factor receptor-related transmembrane protein. Mass spectrometry and especially MALDI IMS therefore are not well suited to directly detect HER2 because the typical observation mass range for MALDI IMS technology is between 2.4 to 25 ku, well below the 185 ku molecular weight of the epidermal growth factor receptor-related transmembrane protein. In addition, the HER2 is not typically found in body fluids due to the activity of proteases. The method, therefore, may be used to detect protein profiles of HER2 "surrogate markers". These marker proteins may be co-expressed proteins with low molecular weights, fragments of HER2 or other high molecular weight proteins, CRIP1 variants, or other proteins from the HER2 signaling pathway. In contrast to gene transcription experiments, the amounts of CRIP1 and at least one CRIP1 variant or the amounts of more than one CRIP1 variant may be measured to obtain reliable results.

The sample provided by the subject (e.g., a human patient) may be a body fluid (e.g., whole blood, plasma, serum, nipple aspirate fluid, cerebrospinal fluid or urine), a homogenized or extracted tissue, a lysate of a homogenized sample or a tissue section. When the sample is a tissue section, amounts of the marker proteins can be directly measured using imaging mass spectrometry with, for example, matrix assisted laser desorption/ionization (see step 402 in FIG. 17). The amounts of marker proteins, CRIP1 and/or one or more of CRIP1 variants in a sample may be measured by a mass spectrometer and/or a tandem mass spectrometer; e.g., by multiple reaction monitoring (MRM) following state of the art procedures. The tandem mass spectrometry further enables the identification of the measured proteins, which can increase the accuracies of the methods. In addition, the amounts of CRIP1 and/or one or more of CRIP1 variants can be measured by an immunoassay (an immunohistochemical analysis). The CRIP1 and/or one or more of CRIP1 variants can be extracted from the sample utilizing an antibody or other affinity reagents, such as aptamers or affibodies, which may be specific to the CRIP1 or its variants. While the affinity extraction may be combined with mass spectrometric analysis or tandem analysis, a measurement using IMS advantageously has less time consuming preparation steps, and uses less expensive labeling or affinity reagents.

The aforedescribed methods for determining the expression of the human epidermal growth factor receptor 2 (HER2) of a subject can be utilized in a variety of different manners for disease (e.g., cancer) diagnosis and treatment. For example, the methods may used to diagnose breast cancer, ovarian cancer, stomach cancer, uterine cancer, endometrial carcinoma, prostate cancer, cervical cancer or pancreatic cancer. A positive diagnosis, for example, may be based on an associated up-regulated expression of the human epidermal growth factor receptor 2 compared to healthy subjects. In another example, the methods may be used for qualifying breast cancer, ovarian cancer, stomach cancer, uterine cancer, endometrial carcinoma, prostate cancer, cervical cancer or pancreatic cancer by the determined expression status of the human epidermal growth factor receptor 2. In another example, the methods may be used for predicting a patient response to a cancer drug. A beneficial effect of the drug is predicted where, for example, an up-regulated expression of the human epidermal growth factor receptor 2 is present. In still another example, the methods may be used for predicting a patient response to a treatment with Trastuzumab against cancer, especially breast cancer (see step 406 in FIG. 17). The beneficial effects of Trastuzumab are predicted where, for example, an up-regulated expression of the human epidermal growth factor receptor 2 is present.

According to another aspect of the invention, a method is provided for predicting the response of a cancer patient to a drug. The method includes (a) providing a sample from the patient, (b) measuring amounts of the cystein-rich intestinal protein 1 (CRIP1), one or more variants of the cystein-rich intestinal protein 1, and/or proteolytic digestion products thereof in the sample, and (c) respectively comparing amounts of the variants to control amounts determined from samples of patients responding and not responding to the drug.

According to yet another aspect of the invention, a method is provided for predicting the prognosis of a cancer patient. The method includes (a) providing a sample from the patient, (b) measuring amounts of the cystein-rich intestinal protein 1 (CRIP1), one or more variants of the cystein-rich intestinal protein 1, and/or proteolytic digestion products thereof in the sample, and (c) comparing amounts of the variants to control amounts determined from samples of patients with different prognosis.

According to a further aspect of the invention, a method is provided for diagnosing cancer in a subject. The method includes (a) providing a liquid sample from the subject, (b) measuring the amounts of the cystein-rich intestinal protein 1 (CRIP1), one or more variants of the cystein-rich intestinal protein 1, and/or proteolytic digestion products thereof in the sample, and (c) comparing amounts of the variants to control amounts determined from samples of healthy subjects. The liquid sample can be selected from one of a serum, plasma, whole blood, nipple aspirate fluid, cerebrosinal fluid and urine.

According to still another aspect of the invention, a kit is provided for determining the expression status of the human epidermal growth factor receptor 2, for diagnosing cancer, for predicting the response to a drug and/or for predicting the prognosis of a cancer patient. The kit includes at least one antibody or other affinity reagents, like aptamers or affibodies, which are specific to the human cystein-rich intestinal protein 1 and/or CRIP1 variants and/or internal standards.

Although the present invention has been illustrated and described with respect to several preferred embodiments thereof, various changes, omissions and additions to the form and detail thereof, may be made therein, without departing from the spirit and scope of the invention.

What is claimed is:

1. A method for determining an expression of human epidermal growth factor receptor 2 (HER2) of a subject to determine an appropriate breast cancer treatment, comprising:
providing a breast cancer sample from the subject;
measuring amounts of two proteins by mass spectrometry, wherein the two proteins have a molecular weight of 8404 atomic mass units and 8419 atomic mass units, respectively, the molecular weights being assigned to the human cysteine-rich intestinal protein 1 (CRIP1) and a structurally modified variant human cysteine-rich intestinal protein 1, respectively;
comparing the amounts of the proteins to control amounts;
determining the expression of the human epidermal growth factor receptor 2 to be up-regulated if the amounts of the two proteins compared to the control amounts are increased;
and predicting a beneficial effect to Trastuzumab when there is an up-regulated expression of the human epidermal growth factor receptor 2.

2. The method of claim 1, where the amount of at least one further protein is measured by mass spectrometry and compared to a control amount, the at least one protein having a molecular weight substantially equal to 8435, 8450 or 8465 atomic mass units is classified as being related to the one or more variants of the human cysteine-rich intestinal protein 1, wherein expression of the human epidermal growth factor receptor 2 is determined as up-regulated if the amount of the at least one further protein compared to the control amount is increased.

3. The method of claim 1, where the structurally modified variant comprises at least one of an in vivo or in vitro modification, a post-translational modification, a sequence variation, and a point mutation.

4. The method of claim 1, where the two proteins are measured and identified using tandem mass spectrometry.

5. The method of claim 1, where the human cysteine-rich intestinal protein 1 is modified by one or more structural variations, or modified by at least one mutation.

6. The method of claim 5, where the one or more structural variations comprise at least one of disulfide bond formation, one or more methyl groups, and oxygen atoms.

7. The method of claim 5, where at least one of modifications and mutations is located in a core region of the human cysteine-rich intestinal protein 1.

8. The method of claim 1, where the proteins are extracted from the sample, between the steps of providing the sample and measuring the amounts of proteins in the sample, utilizing an antibody or other affinity reagents.

9. The method of claim 8, where the antibody or other affinity reagents comprises aptamers or affibodies, which are specific for the human cysteine-rich intestinal protein 1 or its variants.

10. The method of claim 1, where the breast cancer sample of the subject is homogenized tissue or extracted tissue.

11. The method of claim 10, where the homogenized or extracted tissue comprises one of a lysate of a homogenized tissue, and a tissue section.

12. The method of claim 11, where the tissue section is analyzed using an imaging mass spectrometer.

13. The method of claim 12, where the imaging mass spectrometer comprises a matrix assisted laser desorption/ionization imaging mass spectrometer.

14. The method of claim 1, wherein the amount of at least one further protein is measured by mass spectrometry and compared to a control amount, the at least one further protein having a molecular weight substantially equal to 4740, 8455, 8570, 8607 or 8626 atomic mass units and being classified as being related to fragments of the human epidermal growth factor receptor 2.

15. A method for determining an expression of human epidermal growth factor receptor 2 (HER2) of a subject, comprising:
providing a sample from the subject;
measuring amounts of two proteins by mass spectrometry, wherein the two proteins have a molecular weight of 8404 atomic mass units and 8419 atomic mass units, respectively, the molecular weights being assigned to the human cysteine-rich intestinal protein 1 (CRIP1) and a structurally modified variant human cysteine-rich intestinal protein 1, respectively;
comparing the amounts of the proteins to control amounts; and
determining the expression of the human epidermal growth factor receptor 2 to be up-regulated if the amounts of the two proteins compared to the control amounts are increased.

16. The method of claim 15, where the amount of at least one further protein is measured by mass spectrometry and compared to a control amount, the at least one protein having a molecular weight substantially equal to 8435, 8450 or 8465 atomic mass units is classified as being related to variants of the human cysteine-rich intestinal protein 1, wherein the expression of the human epidermal growth factor receptor 2 is determined as up-regulated if the amount of the at least one further protein compared to the control amount is increased.

17. The method of claim 15, where the proteins are extracted from the sample, between the steps of providing the sample and measuring the amounts of proteins in the sample, utilizing an antibody or other affinity reagents.

18. The method of claim 15, where the sample of the subject comprises one of a body fluid, homogenized tissue and extracted tissue.

19. The method of claim 15, where the sample of the subject is a tissue section.

20. The method of claim 19, where the tissue section is analyzed using an imaging mass spectrometer.

21. The method of claim 15, where the amount of at least one further protein is measured by mass spectrometry and compared to a control amount, the at least one further protein having a molecular weight substantially equal to 4740, 8455, 8570, 8607 or 8626 atomic mass units and being classified as being related to fragments of the human epidermal growth factor receptor 2.

* * * * *

UNITED STATES PATENT AND TRADEMARK OFFICE
CERTIFICATE OF CORRECTION

PATENT NO. : 9,164,098 B2
APPLICATION NO. : 12/879619
DATED : October 20, 2015
INVENTOR(S) : Christian Albers et al.

Page 1 of 1

It is certified that error appears in the above-identified patent and that said Letters Patent is hereby corrected as shown below:

Specification

Column 3
Line 24, please delete "deter mined" and insert -- determined --

Column 7
Line 4, please delete "in/z 8607" and insert -- m/z 8607 --

Column 9
Line 12, please delete "amazon ETD Ion Trap" and insert -- amaZon ETD Ion Trap --

Signed and Sealed this
Twenty-third Day of February, 2016

Michelle K. Lee
*Director of the United States Patent and Trademark Office*